US010265487B2

(12) United States Patent
Booth Wise et al.

(10) Patent No.: US 10,265,487 B2
(45) Date of Patent: Apr. 23, 2019

(54) OXYGENATION MASK WITH INTEGRATED END-TIDAL CARBON DIOXIDE MONITORING

(71) Applicant: B&T HEALTHCARE SOLUTIONS LLC, Atlanta, GA (US)

(72) Inventors: LaToya Booth Wise, Atlanta, GA (US); Taj Eubanks, Atlanta, GA (US)

( * ) Notice: Subject to any disclaimer, the term of this patent is extended or adjusted under 35 U.S.C. 154(b) by 0 days.

(21) Appl. No.: 14/955,164

(22) Filed: Dec. 1, 2015

(65) Prior Publication Data

US 2017/0151406 A1    Jun. 1, 2017

(51) Int. Cl.
*A61M 16/06* (2006.01)
*A61M 16/10* (2006.01)
(Continued)

(52) U.S. Cl.
CPC ............ *A61M 16/06* (2013.01); *A61B 5/082* (2013.01); *A61M 16/049* (2014.02);
(Continued)

(58) Field of Classification Search
CPC ............ A61M 15/0086; A61M 15/009; A61M 16/00; A61M 16/0051; A61M 16/0075; A61M 16/0078; A61M 16/009; A61M 16/04; A61M 16/0461; A61M 16/0463; A61M 16/0488; A61M 16/0493; A61M 16/06; A61M 16/0605; A61M 16/0616; A61M 16/0666; A61M 16/0672; A61M 16/0683; A61M 16/0688; A61M 16/08; A61M 16/0808; A61M 16/0816; A61M 16/0825; A61M 16/0833; A61M 16/085; A61M 16/0875; A61M 16/10; A61M 16/1005; A61M 16/105; A61M 16/12; A61M 16/125; A61M 16/127; A61M 16/16; A61M 16/208; A61M 2016/0042;
(Continued)

(56) References Cited

U.S. PATENT DOCUMENTS 803,475 A * 10/1905 Dennis ................. A61C 19/063
                                                        433/140
2,625,155 A * 1/1953 Engelder ............... A61M 16/06
                                                        128/206.24
(Continued)

FOREIGN PATENT DOCUMENTS

WO    WO 2008/153830 A1    12/2008

*Primary Examiner* — Annette Dixon
(74) *Attorney, Agent, or Firm* — Alston & Bird LLP

(57) ABSTRACT

Various embodiments are directed to oxygenation masks having a plurality of tubes detachably secured to the oxygenation mask, wherein the plurality of tubes comprise an oxygen tube configured to supply oxygen gas received from an oxygen source to the patient via the oxygenation mask and an end-tidal carbon dioxide return tube configured to direct a portion of the patient's exhaled breath, comprising carbon dioxide, away from the oxygenation mask and to an end-tidal CO2 monitoring device. Accordingly, the oxygenation mask may be configured to supply oxygen to a patient while concurrently monitoring the breath metabolism rate of the patient by collecting a portion of the patient's exhaled breath in a gas return tube which is in fluid communication with an ETCO2 monitoring system.

8 Claims, 4 Drawing Sheets

(51) Int. Cl.
*A61M 16/08* (2006.01)
*A61B 5/08* (2006.01)
*A61M 16/04* (2006.01)
*A61M 16/00* (2006.01)
*A61M 16/20* (2006.01)
*A61M 16/12* (2006.01)

(52) U.S. Cl.
CPC ........ *A61M 16/085* (2014.02); *A61M 16/104* (2013.01); *A61M 16/0078* (2013.01); *A61M 16/125* (2014.02); *A61M 16/208* (2013.01); *A61M 2202/0208* (2013.01); *A61M 2205/05* (2013.01); *A61M 2230/432* (2013.01)

(58) Field of Classification Search
CPC .. A61M 2016/1025; A61M 2202/0007; A61M 2202/0208; A61M 2205/0205; A61M 2205/0227; A61M 2205/0238; A61M 2205/18; A61M 2205/3344; A61M 2205/3569; A61M 2205/50; A61M 2205/582; A61M 2205/583; A61M 2205/584; A61M 2205/6045; A61M 2206/22; A61M 2209/06; A61M 2209/08; A61M 2209/088; A61M 2210/005; A61M 2210/0618; A61M 2210/0625; A61M 2230/205; A61M 2230/43; A61M 2230/432; A61M 2230/435; A61M 39/1011; A61M 39/1055; A62B 18/02; A62B 7/14; A62B 9/006
USPC ........... 128/200.11, 200.14, 200.18, 200.21, 128/200.24, 202.27, 203.12, 203.28, 128/203.29, 204.18, 204.23, 205.12, 128/205.13, 205.17, 205.24, 205.25, 128/205.27, 206.12, 206.13, 206.15, 128/206.18, 206.21, 206.24, 206.26, 128/206.28, 207.12, 207.13, 861; 600/531, 532
See application file for complete search history.

(56) References Cited

U.S. PATENT DOCUMENTS

| | | | |
|---|---|---|---|
| 2,669,988 A * | 2/1954 | Carpenter | A61B 1/24 128/861 |
| 4,030,493 A * | 6/1977 | Walters | A61M 16/0488 128/206.21 |
| 4,201,205 A | 5/1980 | Bartholomew | |
| 4,270,531 A * | 6/1981 | Blachly | A61M 16/0488 128/207.14 |
| 4,328,797 A * | 5/1982 | Rollins, III | A61M 16/06 128/202.15 |
| 4,432,513 A | 2/1984 | Yost | |
| 4,580,556 A | 4/1986 | Kondur | |
| 5,184,609 A | 2/1993 | Hart | |
| 5,273,032 A * | 12/1993 | Borody | A61M 16/0488 128/200.24 |
| 5,300,037 A | 4/1994 | Delk et al. | |
| 5,400,781 A * | 3/1995 | Davenport | A61M 16/06 128/205.25 |
| 5,474,060 A * | 12/1995 | Evans | A61B 5/097 128/204.22 |
| 5,492,114 A | 2/1996 | Vroman | |
| 5,758,642 A * | 6/1998 | Choi | A61M 16/06 128/205.25 |
| 6,032,688 A | 3/2000 | Marshall Byars | |
| 6,386,198 B1 * | 5/2002 | Rugless | A62B 18/10 128/205.25 |
| 6,763,831 B2 | 7/2004 | Sniadach | |
| 8,365,734 B1 * | 2/2013 | Lehman | A61M 16/0078 128/200.24 |
| 2001/0035181 A1 * | 11/2001 | Elkins | A61M 11/06 128/200.21 |
| 2002/0129816 A1 * | 9/2002 | Williams | A61B 1/00154 128/203.12 |
| 2003/0024533 A1 | 2/2003 | Sniadach | |
| 2003/0047188 A1 * | 3/2003 | Mace | A61M 16/06 128/205.25 |
| 2003/0196664 A1 | 10/2003 | Jacobson | |
| 2005/0139220 A1 | 6/2005 | Christopher | |
| 2005/0145247 A1 * | 7/2005 | Nashed | A61M 16/00 128/204.18 |
| 2006/0231091 A1 | 10/2006 | Camarillo | |
| 2007/0006878 A1 * | 1/2007 | Mackey | A61M 16/0488 128/200.26 |
| 2008/0053449 A1 | 3/2008 | Lindblom et al. | |
| 2008/0110456 A1 * | 5/2008 | Flynn | A61M 16/0488 128/200.26 |
| 2009/0275851 A1 | 11/2009 | Colman et al. | |
| 2010/0113880 A1 | 5/2010 | Page | |
| 2011/0100368 A1 | 5/2011 | Taylor-Kennedy | |
| 2011/0108509 A1 | 5/2011 | Fontana | |
| 2012/0330111 A1 | 12/2012 | Borody | |
| 2013/0060157 A1 * | 3/2013 | Beard | A61M 16/06 600/532 |
| 2013/0172768 A1 | 7/2013 | Lehman | |
| 2014/0128676 A1 * | 5/2014 | Law | A61M 16/06 600/114 |
| 2014/0243698 A1 * | 8/2014 | Koch | A61M 16/085 600/531 |
| 2014/0276171 A1 * | 9/2014 | Hestness | A61B 5/097 600/531 |
| 2015/0217075 A1 * | 8/2015 | Nair | A61M 16/085 600/531 |
| 2016/0038709 A1 * | 2/2016 | Beard | A61B 5/097 128/205.12 |

\* cited by examiner

OXYGENATION MASK WITH INTEGRATED END-TIDAL CARBON DIOXIDE MONITORING

TECHNOLOGICAL FIELD

Example embodiments of the invention relate generally to oxygen masks and more particularly to improved oxygen masks for monitoring patient health conditions.

BACKGROUND

Medical patients may receive a constant and/or monitored supply of oxygen during medical treatment. For example, patients undergoing surgery and/or medical patients having medical conditions which make breathing difficult (e.g., patients having Chronic Obstructive Pulmonary Disease (COPD), Mesothelioma, obesity, and/or the like) may be provided with a monitored and/or constant supply of oxygen while receiving medical treatment.

Because patients receiving supplied oxygen may have difficulty breathing and/or may be undergoing surgery, such oxygen is generally supplied to patients via a mask configured to facilitate breathing for the patient. Accordingly, oxygen supply masks often cover both the nose and mouth of the patient in order to permit the patient to breathe through either orifice. Thus, access to both the patient's nose and mouth are significantly impeded once the mask is positioned over the patient's face. Due to the positioning of the oxygenation mask over both the patient's nose and mouth, the oxygenation mask may impede positioning of medical equipment around the patient's nose and mouth.

Certain oxygenation masks have sought to improve access to the patient's nose and mouth by providing access openings extending through a portion of mask such that medical equipment may be extended through one or more access openings for monitoring oxygen. Although such masks may facilitate placement of certain medical devices through the mask for monitoring oxygen, these masks typically do not fully address the difficulties in placing other commonly used medical monitoring devices into the mask for monitoring other gases.

Accordingly, an improved oxygenation mask is needed for providing increased patient comfort while providing improved monitoring of patient health conditions through the oxygenation mask.

BRIEF SUMMARY

Various exemplary embodiments provide improved medical monitoring of a patient's breathing through an oxygenation mask having integrated breathing monitoring mechanisms. Because the oxygenation mask incorporates a breathing monitoring mechanism, the mask provides improved patient comfort because monitoring of the patient's breathing does not require a separate monitoring mechanism to be placed around the patient's nose and/or mouth in addition to the oxygenation mask.

Various exemplary embodiments are directed to oxygenation masks (e.g., a simple oxygenation mask, a rebreather oxygenation mask, and/or a partial rebreather oxygenation mask) for monitoring a patient's breathing during a medical procedure. In various exemplary embodiments, an oxygenation mask may include a facial enclosure configured to enclose a patient's nose and mouth, and an oxygen supply tube configured to supply oxygenated air to the facial enclosure. The oxygenation mask may also include an end-tidal carbon dioxide return tube configured to direct a portion of a patient's exhaled breath, comprising carbon dioxide, away from the facial enclosure to an end-tidal carbon dioxide monitoring device to enable the end-tidal carbon dioxide monitoring device to detect an exhaled concentration or partial pressure of the carbon dioxide during the medical procedure. In various exemplary embodiments, the facial enclosure may define one or more ventilation ports configured to allow gas to pass out of the facial enclosure to a surrounding environment, wherein the one or more ventilation ports are configured to permit a portion of the patient's exhaled breath to escape from within the facial enclosure. The oxygenation mask may also include a tube engagement member configured to detachably secure a plurality of tubes to the facial enclosure such that each of the plurality of tubes are in fluid communication with the interior of the facial enclosure. In various exemplary embodiments, the facial enclosure may further define one or more access ports configured to permit an object to be passed into the interior of the facial enclosure when positioned over a patient's face. Moreover, each access port may be associated with a corresponding plug configured to engage a perimeter of a corresponding access port and block the access port. In various exemplary embodiments, the oxygen supply tube may be connected to the gas return tube along a portion of the length of the oxygen supply tube.

In various exemplary embodiments, the tube engagement member may correspond to a single gas port extending through the facial enclosure, and the oxygen supply tube and the gas return tube may both be in fluid communication with the interior of the oxygenation mask through the single gas port. Moreover, in various exemplary embodiments, the gas return tube may be in fluid communication with an end-tidal carbon dioxide monitoring system.

In various exemplary embodiments, the tube engagement member may be positioned on the facial enclosure such that the tube engagement member is below the patient's nose in an instance in which the facial enclosure is secured on the patient's face. In certain exemplary embodiments, the tube engagement member may be positioned on the facial enclosure closer to a bottom portion of the facial enclosure than a top portion of the facial enclosure.

Additionally, various exemplary embodiments are directed to an oxygenation mask for monitoring a patient's breathing during a medical procedure. In exemplary various embodiments, the oxygenation mask may include a mouthpiece configured to be placed within a patient's mouth and prevents a patient from closing the patient's mouth, wherein the mouthpiece defines one or more gas channels extending through the mouthpiece to permit the patient to breathe air through the one or more gas ports. The oxygenation mask may also include a gas fitting secured to the mouthpiece proximate an exterior opening of the one or more gas channels and is configured to place one or more gas tubes in fluid communication with the one or more gas channels. The low-profile oxygenation mask may also include an oxygen supply tube in fluid communication with the gas fitting and is configured to direct oxygen gas into the patient's mouth through the one or more gas channels. The oxygenation mask may also include an end-tidal carbon dioxide return tube in fluid communication with the gas fitting and is configured to collect a portion of a patient's exhaled breath, comprising carbon dioxide, from a stream of air passing out of the patient's mouth through the one or more gas channels. In various exemplary embodiments, the mouthpiece may be configured to rest between a patient's upper teeth and lower teeth when positioned in the patient's mouth.

Moreover, in some exemplary embodiments, the gas fitting may include one or more nozzles extending into the one or more gas ports. Additionally, in some exemplary embodiments, the gas return tube may by in fluid communication with an end-tidal carbon dioxide monitoring system. Moreover, the oxygen supply tube may be connected to the gas return tube along a portion of the length of the oxygen supply tube.

BRIEF DESCRIPTION OF THE SEVERAL VIEWS OF THE DRAWINGS

Reference will now be made to the accompanying drawings, which are not necessarily drawn to scale, and wherein.

DETAILED DESCRIPTION

The present invention will now be described more fully hereinafter with reference to the accompanying drawings, in which some, but not all embodiments of the invention are shown. Indeed, the invention may be embodied in many different forms and should not be construed as limited to the embodiments set forth herein. Rather, these embodiments are provided so that this disclosure will satisfy applicable legal requirements. Like numbers refer to like elements throughout.

Various exemplary embodiments provide an oxygenation mask for a medical patient having improved access to the patient's nose and mouth and having integrated End-Tidal Carbon Dioxide (ETCO2) monitoring mechanisms. Accordingly, a patient's lung metabolism may be monitored via the integrated ETCO2 monitoring mechanism without requirement bulky additional monitoring equipment to be placed around and/or into the oxygenation mask while it is positioned over a patient's face.

Oxygenation Facemask with Medical Device Access

Figure 1:
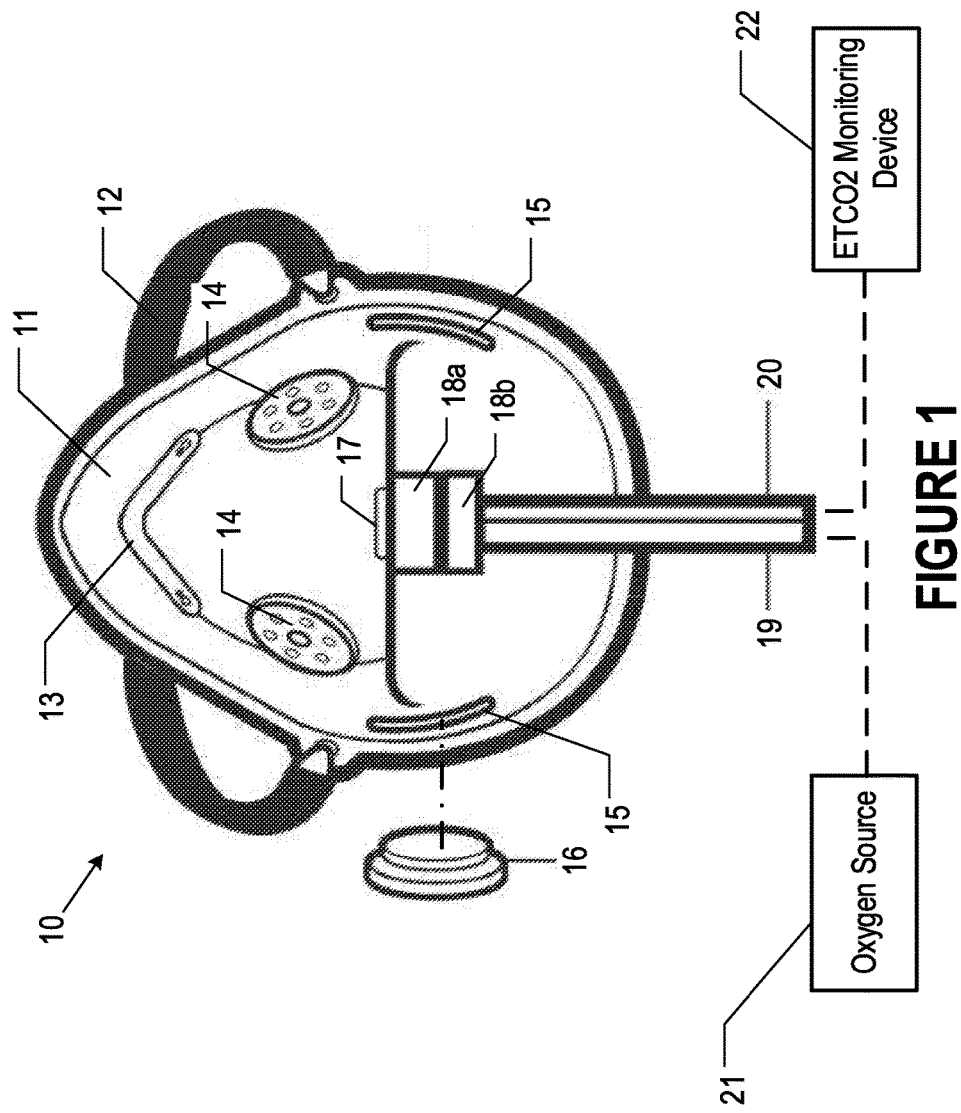
FIG. 1 shows a front view of an oxygenation mask according to one exemplary embodiment.

FIG. 1 shows a front view of a simple oxygenation mask for supplying oxygen and ETCO2 to a patient according to an exemplary embodiment. In the illustrated example embodiment of FIG. 1, the oxygenation mask 10 includes a facial enclosure 11 having an open backside configured such that a patient's nose and mouth may fit within the facial enclosure 11. Accordingly, when placed over a patient's face, the facial enclosure 11, together with the patient's face, forms an enclosed volume in which the patient's nose and mouth are positioned. In some exemplary embodiments, the facial enclosure 11 may include a flexible plastic material configured to flex and thereby contour to the patient's face around the patient's nose and mouth to securely rest against the patient's face. By contouring to the patient's face, the facial enclosure 11 may avoid providing any sharp edges which may cause discomfort for the patient. In various embodiments, the facemask may include a rigid material, and may have a flexible resilient edge guard (e.g., a cushion) surrounding an edge of the facial enclosure 11. The resilient edge guard may accordingly provide a comfortable edge of the facial enclosure 11 which contours to the shape of the patient's face such that the facial enclosure 11 does not cause discomfort for the patient.

With reference again to FIG. 1, the illustrated example embodiment of the oxygenation mask 10 additionally includes a securing strap 12 configured to secure the oxygenation mask 10 onto the patient. As shown in FIG. 1, the securing strap 12 may be secured proximate opposite sides of the facial enclosure 11 and may be configured to extend around a patient's head to secure the oxygenation mask 10 onto the patient's face. Accordingly, the securing strap 12 may have an adjustable length (e.g., having a buckle assembly and/or the like) in order to accommodate various patient sizes. Moreover, in some example embodiments, the securing strap 12 may include an elastic material configured to stretch in an instance in which the securing strap 12 is placed around a patient's head and to thereby provide a slight return force to maintain the positioning of the oxygenation mask 10 relative to the patient.

Moreover, as shown in FIG. 1, the oxygenation mask may include a nose bridge clamp 13 to facilitate placement of the oxygenation mask 10 relative to the patient's nose. In some example embodiments, the nose bridge clamp 13 may include a bendable and formable material (e.g., a metal material) configured to permit the nose bridge clamp 13 to be bent to conform to the shape of the patient's nose, and to maintain the bent shape of the nose bridge clamp 13. In the illustrated example embodiment of FIG. 1, the nose bridge clamp 13 is positioned proximate a top portion of the facial enclosure 11 such that the nose bridge clamp 13 is positioned adjacent to the patient's nose bridge in an instance in which the oxygenation mask 10 is secured onto the patient's face. Accordingly, the nose bridge clamp 13 may be configured to be bent to conform to the shape of the patient's nose bridge to provide a secure and comfortable positioning of the oxygenation mask 10 relative to the patient's face.

As shown in FIG. 1, an exemplary embodiment of the oxygenation mask 10 may additionally include one or more ventilation ports which may permit air to be exchanged between the interior of the facial enclosure 11 and the surrounding environment. For example, as shown in FIG. 1, the facial enclosure may define one or more exhalation valves 14 configured to selectably permit air within the enclosure formed by the facial enclosure 11 to be released from within the enclosure and into the surrounding environment. Accordingly, in an example embodiment, the exhalation valves 14 may each include a one-way valve configured to selectably permit air to escape from within the oxygenation mask 10. In some example embodiments, the exhalation valves 14 may be configured to permit air to escape from within the enclosure formed by the facial enclosure 11 only upon a determination that an air pressure exerted on the exhalation valves 14 from within the facial enclosure 11 exceeds some predefined threshold pressure value. For example, the exhalation valves 14 may be configured such that the pressure within the facial enclosure 11 caused by supplying pressurized oxygen (as described in greater detail herein) to the oxygenation mask 10 is insufficient to open the exhalation valves 14 to release the air from within the facial enclosure 11 to the surrounding environment. However, the increased pressure within the facial enclosure 11 caused by a patient's exhaled breath may be sufficient to operate the exhalation valves 14 and thereby release at least a portion of the air within the facial enclosure 11 to the surrounding environment.

In an example embodiment as shown in FIG. 1, the ventilation ports may include one or more access ports 15 extending through the facial enclosure 11. These access ports 15 may permit the exchange of air through the oxygenation mask 10 like the exhalation valves 14. Such access ports 15 may provide access for one or more medical devices (e.g., an endoscope, a probe, etc.) to be positioned through the oxygenation mask 10 without causing additional discomfort to the patient. For the sake of comparison, without an access port 15 extending through the oxygenation mask 10, medical professionals may be required to place an endoscope or other medical device between an edge of the oxygenation mask 10 and a patient's face, which may cause significant discomfort to the patient because the medical device may be pressed against the patient's face by edges of the oxygenation mask 10.

In an example embodiment, the access port 15 (also referred to herein as access openings 15) may have any of a variety of shapes, including round, square, triangular and/or the like. The access ports 15 may have a slit extending through the facial enclosure 11. Moreover, as illustrated in FIG. 1, various embodiments additionally comprise a plug 16 corresponding to one or more of the access openings 15. The plug 16 may have a shape corresponding to the shape of the access opening 15, and may be configured to engage edges of the access opening 15 such that the plug remains securely positioned within the access opening 15. Furthermore, in some example embodiments, the plug 16 may include a flexible material (e.g., a plastic material, a rubber material, and/or the like). In exemplary embodiments in which the facial enclosure 11 includes a rigid material, a flexible plug 16 may facilitate placement of the plug within the access openings 15. However, in some other exemplary embodiments, the plug 16 may comprise a rigid material (e.g., plastic). In example embodiments in which the facial enclosure 11 includes a flexible material, a rigid plug 16 may be configured to be securely positioned within the access openings 15. Accordingly, the plug 16 may be configured such that air cannot freely flow through the access opening 15 in an instance in which a medical device is not positioned therein.

As shown in FIG. 1, the oxygenation mask 10 may additionally include one or more gas ports 17 through which oxygen and/or carbon dioxide flows during use. In some example embodiments, the oxygenation mask 10 may have a single gas port 17 configured to permit oxygen to flow into the mask and carbon dioxide to flow out of the mask. However, in other example embodiments, the oxygenation mask 10 may have one or more gas ports 17 corresponding to each designated gas flow (e.g., inflow and outflow). For example, the oxygenation mask 10 may have an input gas port 17 corresponding to an oxygen supply, and an output gas port 17 corresponding to a carbon dioxide return (as described in greater detail herein). In the illustrated example embodiment of FIG. 1, the gas port 17 is positioned proximate a mid-portion of the oxygenation mask 10, such that a patient's breath is directed toward the gas port 17. In various embodiments, the gas port 17 may be located closer to a bottom portion of the mask (e.g., proximate a portion of the mask 10 that engages a patient's chin when worn by the patient) than a top portion of the mask 10 (e.g., proximate a portion of the mask 10 that engages a patient's face above the patient's nostrils). The positioning of the gas port 17 may permit an effective exchange of oxygen and carbon dioxide between the oxygen source, the patient, and the ETCO2 monitoring system 22 (also referred to herein as ETCO2 monitoring device 22). For example, the gas port 17 may be positioned such that the gas port 17 is proximate the patient's mouth and nostrils when the oxygenation mask 10 is positioned over the patient's face. Thus, the patient's breath (e.g., whether from his or her nose or mouth) is directed toward the gas port 17 during exhalation.

As shown in FIG. 1, the gas port 17 may be associated with one or more tube engagement members, such as one or more gas fittings 18a configured to permit one or more gas mechanisms to be secured relative to the oxygenation mask 10. For example, and as illustrated in FIG. 1, the gas fitting 18a may be configured to engage a corresponding tube fitting 18b which defines an end of one or more gas hoses such that the gas hoses may be secured to the oxygenation mask 10. As a specific example, an oxygen source 21 may be placed in fluid communication with the interior of the facial enclosure 11 via an oxygen hose 19 secured to the gas fitting 18a such that oxygen may flow between the oxygen source 21 and the interior of the facial enclosure 11. Accordingly, pressurized oxygen may be supplied to the patient through the oxygenation mask 10 via the oxygen hose 19 secured to the gas fitting 18. Moreover, as shown in FIG. 1, a gas return hose 20 may additionally be secured to the oxygenation mask 10 via the gas fitting 18a. In various embodiments, the gas return hose 20 (also referred to herein as ETCO2 return hose 20) may place the interior of the oxygenation mask 10 in fluid communication with an ETCO2 monitoring system 22 (e.g., a capnograph) configured to monitor the lung metabolism of a patient and/or to monitor inhaled and exhaled concentration or partial pressure of carbon dioxide ($CO_2$) in a respiratory gas and/or indirectly monitor the $CO_2$ partial pressure in arterial blood, for example, during anesthesia and other medical procedures (e.g. intensive care procedures). As shown in FIG. 1, the oxygen hose 19 and the gas return hose 20 may be secured with a single hose fitting 18b such that the oxygen hose 19 and the gas return hose 20 each terminate at a common volume located within the single hose fitting 18b. For example, although not shown in FIG. 1, the single hose fitting 18b may define two hose connection points (e.g., hose barbs), each corresponding to one of the oxygen hose 19 or the gas return hose 20. The single hose fitting 18b may be an air tight fitting secured such that gases (e.g., oxygenated air and/or a patient's exhaled breath) cannot escape into the surrounding environment between and/or around either of the attached hoses 19, 20. Moreover, in various exemplary embodiments, the hose fitting 18b may be configured to be detachably secured with the gas fitting 18a (e.g., via a threaded connection, a snap connection, a barbed connection, and/or the like) such that the interior of the hoses 19, 20 is in fluid communication with the interior of the facial enclosure 11 to allow the exchange of gases between the hoses 19, 20 and the interior of the facial enclosure 11. However, in various embodiments, the hose fitting 18b may be secured relative to the gas fitting 18a such that the fittings cannot be detached. Although the illustrated embodiment of FIG. 1 shows the gas return hose 20 being secured to the oxygenation mask 10 via a common gas fitting 18a shared with the oxygen hose 19, various exemplary embodiments may secure the return hose 20 via a separate gas fitting 18.

By providing an ETCO2 return hose 20 secured directly to the oxygenation mask 10 such that at least a portion of a patient's breath may be captured within the gas return hose 20 and directed to ETCO2 monitoring device 22, a patient's lung metabolism may be monitored without a separate monitoring device secured to the patient to collect the patient's breath. In this regard, a separate nasal cannula may not need to be provided for the patient in order to obtain a sufficient percentage of the patient's exhalation breath to accurately monitor the patient's lung metabolism rate. By providing the ETCO2 return hose 20 secured directly to the oxygenation mask 10 (via fittings 18a, 18b), a patient's comfort may be improved because no additional monitoring devices need be secured to the patient in addition to the oxygenation mask 10. Moreover, in various embodiments, by directly connecting the ETCO2 return hose 20 to the facial enclosure 11, a sufficient amount of a patient's exhaled breath may be collected for monitoring of the patient's ETCO2 in a mask(s) (e.g., oxygenation mask 10) in which at least a portion of the patient's exhaled breath escapes into the surrounding environment.

Non-Rebreathing Oxygenation Facemask

Figure 2:
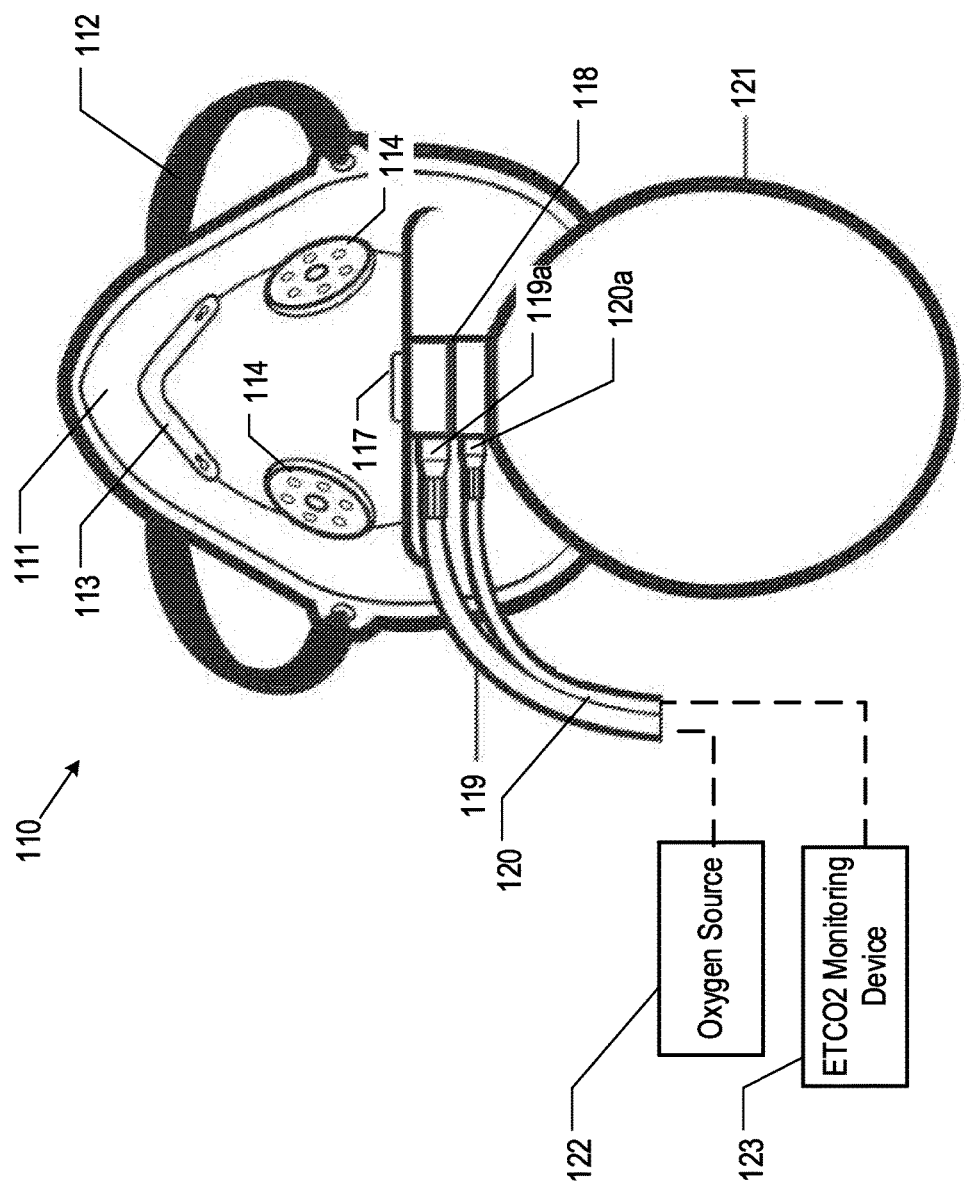
FIG. 2 shows a front view of an oxygenation mask having an oxygen supply bag according to one exemplary embodiment.

FIG. 2 illustrates an example embodiment of a non-rebreathing oxygenation facemask having a breath metabolism mechanism incorporated therein. In the illustrated embodiment of FIG. 2, the oxygenation mask 110 includes a facial enclosure 111 having an open backside configured such that a patient's nose and mouth may fit within the facial enclosure 111. Accordingly, when placed over a patient's face, the facial enclosure 111 forms an enclosed volume in which the patient's nose and mouth are positioned. In various example embodiments, the facial enclosure 111 may include a flexible plastic material configured to flex and thereby contour to the patient's face around the patient's nose and mouth to securely rest against the patient's face. By contouring to the patient's face, the facial enclosure 111 may avoid providing any sharp edges which may cause discomfort for the patient. In an example embodiment, the oxygenation mask 110 may include a rigid material, and may have a resilient edge guard surrounding an edge of the facial enclosure 11. The resilient edge guard may accordingly provide a comfortable edge of the facial enclosure 111 which contours to the shape of the patient's face such that the facial enclosure 111 does not cause discomfort for the patient.

With reference again to FIG. 2, the illustrated example embodiment of the oxygenation mask 110 may additionally include a securing strap 112 configured to secure the oxygenation mask 110 onto the patient. As shown in FIG. 2, the securing strap 112 may be secured proximate opposite sides of the facial enclosure 111 and may be configured to extend around a patient's head to secure the oxygenation mask 110 onto the patient's face. Accordingly, the securing strap 112 may have an adjustable length (e.g., having a buckle assembly and/or the like) in order to accommodate various patient sizes. Moreover, in various example embodiments, the securing strap 112 may include an elastic material configured to stretch when placed around a patient's head and to thereby provide a slight return force to maintain the positioning of the oxygenation mask 110 relative to the patient.

Moreover, as shown in FIG. 2, the oxygenation mask 110 may include a nose bridge clamp 113 to facilitate placement of the oxygenation mask 110 relative to the patient's nose. In some example embodiments, the nose bridge clamp 113 may include a bendable and formable material (e.g., a metal material) configured to permit the nose bridge clamp 113 to be bent to conform to the shape of the patient's nose, and to maintain the bent shape of the nose bridge clamp 113. In the illustrated example embodiment of FIG. 2, the nose bridge clamp 113 is positioned proximate a top portion of the facial enclosure 111 such that the nose bridge clamp 113 is positioned adjacent to the patient's nose bridge in an instance in which the oxygenation mask 110 is secured onto the patient's face. Accordingly, the nose bridge clamp 113 may be configured to be bent to conform to the shape of the patient's nose bridge to provide a secure and comfortable positioning of the oxygenation mask 110 relative to the patient's face.

As shown in FIG. 2, various embodiments of the oxygenation mask 110 may additionally include one or more ventilation ports (e.g., one or more exhalation valves 114) which permit air to be exchanged between the interior of the facial enclosure 111 and the surrounding environment. For example, as shown in FIG. 2, the facial enclosure may define one or more exhalation valves 114 configured to selectably permit air within the enclosure formed by the facial enclosure 111 to be released from within the enclosure and into the surrounding environment. Accordingly, in various example embodiments, the exhalation valves 114 may each include a one-way valve configured to selectably permit air to escape from within the oxygenation mask 110. In various example embodiments, the exhalation valves 114 may be configured to permit air to escape from within the enclosure formed by the facial enclosure 111 only upon a determination that an air pressure exerted on the exhalation valves 114 from within the facial enclosure 11 exceeds some predefined threshold pressure value. For example, the exhalation valves 114 may be configured such that the pressure within the facial enclosure 111 caused by supplying pressurized oxygen (as described in greater detail herein) to the oxygenation mask 110 is insufficient to open the exhalation valves 114 to release the air from within the facial enclosure 111 to the surrounding environment. However, the increased pressure within the facial enclosure 111 caused by a patient's exhaled breath may be sufficient to operate the exhalation valves 114 and thereby release at least a portion of the air within the facial enclosure 111 to the surrounding environment.

In the illustrated embodiment of FIG. 2, the oxygenation mask 110 may include an oxygen bag 121 in fluid communication with the interior of the facial enclosure 111 configured to inflate when oxygen is flowing into the mask such that air may be exchanged between the interior of the oxygen bag 121 and the interior of the facial enclosure 111. Accordingly, as oxygen is supplied to the oxygenation mask 110 (e.g., via an oxygen hose 119 in fluid communication with an oxygen source 122 to allow oxygen to flow between the oxygen source 122 and the oxygenation mask 110, described in detail herein), unused oxygen may collect in the oxygen bag 121 before being directed into the facial enclosure 111.

As shown in FIG. 2, the oxygenation mask 110 may additionally define one or more gas ports 117 through which oxygen and/or carbon dioxide flows during use. In various embodiments, the oxygenation mask 110 may have a single gas port 117 configured to permit oxygen to flow into the mask, and carbon dioxide to flow out of the mask. However, in various embodiments, the oxygenation mask 110 may have one or more gas ports 117 corresponding to each designated gas flow (e.g., inflow and outflow). For example, the oxygenation mask 110 may have an input gas port 117 corresponding to an oxygen supply 122, and an output gas port 117 corresponding to a carbon dioxide return (as described in greater detail herein). In the illustrated example embodiment of FIG. 2, the gas port 117 is positioned proximate a mid-portion of the oxygenation mask 110 (e.g., proximate a fluid conduit between the oxygen bag 121 and the facial enclosure 111) such that a patient's breath is directed toward the gas port 117. In various example embodiments, the gas port 117 may be located closer to a bottom portion of the mask (e.g., proximate a portion of the mask 110 that engages a patient's chin when worn by the patient) than a top portion of the mask 110 (e.g., proximate a portion of the mask 110 that engages a patient's face above the patient's nostrils). The positioning of the gas port 117 may permit an effective exchange of oxygen and carbon dioxide between the oxygen source, the patient, and the ETCO2 monitoring system 123 (also referred to herein as ETCO2 monitoring device 123). For example, the gas port 117 may be positioned such that the gas port 117 is proximate the patient's mouth and nostrils when the oxygenation mask 110 is positioned over the patient's face. Thus, the patient's breath (e.g., whether from his or her nose or mouth) is directed toward the gas port 117 during exhalation.

As shown in FIG. 2, the gas port 117 may be associated with one or more tube engagement members, such as a gas fitting 118 configured to permit one or more gas mechanisms to be secured relative to the oxygenation mask 110. For example, and as illustrated in FIG. 2, the gas fitting 118 may provide a detachable fluid conduit between the facial enclosure 111 and the oxygen bag 121 such that the oxygen bag 121 may be detached from the facial enclosure 111. Moreover, as shown in FIG. 2, the gas fitting 118 may be configured to engage an end of one or more gas hoses having corresponding hose fittings 119a, 120a such that the gas hoses may be secured to the oxygenation mask 110. As a specific example, an oxygen source 122 may be placed in fluid communication with the interior of the facial enclosure 111 via an oxygen hose 119 secured to the gas fitting 118 such that oxygen may flow through the oxygen hose 119 between the oxygen source 122 and the interior of the facial enclosure 111. Accordingly, pressurized oxygen may be supplied to the patient through the oxygenation mask 110 via the oxygen hose 119, from the oxygen source 122, secured to the gas fitting 118. Moreover, as shown in FIG. 2, a gas return hose 120 (also referred to herein as ETCO2 return hose 120) may additionally be secured to the oxygenation mask 110 via the gas fitting 118. In various example embodiments, the gas return hose 120 may place the interior of the oxygenation mask 110 in fluid communication with an ETCO2 monitoring system 123 configured to monitor the lung metabolism of a patient and/or to monitor inhaled and exhaled concentration (e.g., 5% to 6% $CO_2$) respiratory gas and/or indirectly monitor the $CO_2$ partial pressure in arterial blood, for example, during anesthesia or other medical procedures (e.g. intensive care procedures). As shown in FIG. 2, each of the oxygen supply hose 119 and the gas return hose 120 may have separate corresponding fittings 119a, 120a that may each be configured to be secured to the gas fitting 118 at separate connection points. For example, the gas fitting 118 may define two connection points 118a, 118b (e.g., threaded connection points, barbed connection points, snap connection points, and/or the like), each corresponding to one of the oxygen supply hose fitting 119a or the gas return hose fitting 120a. Each of the connection points may be configured to place a connected hose (e.g., an oxygen hose 119 or a gas return hose 120) in fluid communication with an interior of the gas fitting 118, which may be in fluid communication with the interior of the facial enclosure 111 to allow the exchange of gases between the hose and the interior of the facial enclosure 111.

In some example embodiments, the oxygen hose 119 and the gas return hose 120 may be secured relative to a single hose fitting, similar to that described in reference to FIG. 1. In such example embodiments, the gas fitting 118 may have a single connection point configured to engage the single hose fitting (e.g., a threaded connection point, a barbed connection point, a snap connection point, and/or the like).

By providing a gas return hose 120 secured directly to the oxygenation mask 110 such that at least a portion of a patient's breath may be captured within the gas return hose 120 and directed to an ETCO2 monitoring system 123, a patient's lung metabolism may be monitored without a separate monitoring device secured to the patient to collect the patient's breath. Indeed, a separate nasal cannula may not need to be provided for the patient in order to obtain a sufficient percentage of the patient's exhalation breath to accurately monitor the patient's lung metabolism rate and/or partial pressure of carbon dioxide ($CO_2$) in a respiratory gas. By providing the ETCO2 return hose 120 secured directly to the oxygenation mask 110 (e.g., via fittings 119a, 120a), a patient's comfort may be improved because no additional monitoring devices need be secured to the patient in addition to the oxygenation mask 110. Moreover, in various embodiments, by directly connecting the ETCO2 return hose 20 to the facial enclosure 111, a sufficient amount of a patient's exhaled breath may be collected for monitoring of the patient's ETCO2 in a mask (e.g., oxygenation mask 110) in which at least a portion of the patient's exhaled breath escapes into the surrounding environment.

Moreover, although not shown in FIG. 2, the facial enclosure 111 may define one or more access ports extending through the facial enclosure 111 and having corresponding plugs similar to those described above in reference to FIG. 1 and facial enclosure 11. Such access ports may provide access for one or more medical devices (e.g., an endoscope, probe, etc. to be positioned through the oxygenation mask 110 and to the patient's mouth or nose) to be positioned through the oxygenation mask 110 without causing additional discomfort to the patient.

Low Profile Oxygenation Facemask

It should be pointed out that during surgical procedures in which a medical professional needs unobstructed access to a patient's nose, oxygenation masks covering the patient's nose may be inappropriate for supplying oxygen to the patient. Example procedures are commonly performed by Ear-Nose-Throat (ENT) medical professionals.

Figure 3:
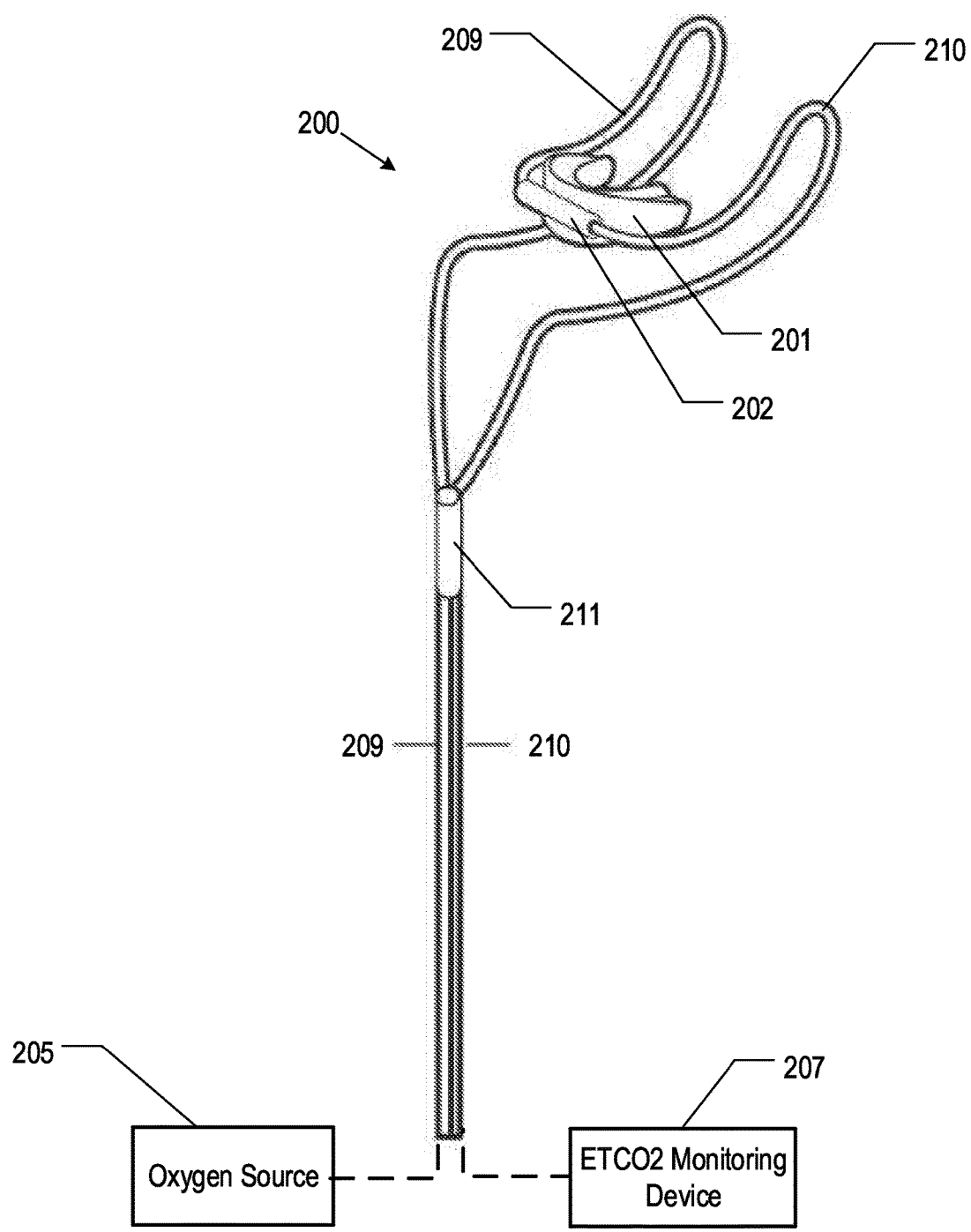
FIG. 3 shows an oxygenation mask configured to provide unobstructed access to a patient's nose according to an exemplary embodiment.

FIG. 3 shows a perspective view of an oxygenation mask providing unobstructed access to a patient's nose. As shown in FIG. 3, the oxygenation mask 200 comprises a mouthpiece 201 secured to one or more gas tubes. In the illustrated example embodiment of FIG. 3, the mouthpiece 201 is configured to fit into a patient's mouth, and may have one or more ridges configured to impede unintended removal of the mouthpiece during a medical procedure. For example, if a patient is asleep (e.g., anesthetized) during a medical procedure, the one or more ridges may be configured to keep the mouthpiece in the patient's mouth during the medical procedure. In the illustrated example embodiment of FIG. 3, the mouthpiece 201 may be generally shaped in a "U"-shape to contour to a patient's teeth, such that the patient may bite down on the mouthpiece 201 while the mouthpiece is located within the patient's mouth. Accordingly, the one or more ridges may define at least a portion of a perimeter of a top surface and/or a bottom surface of the mouthpiece 201, such that a first ridge is located on an interior side of the mouthpiece 201 relative to a patient's teeth (e.g., located behind a patient's teeth when the mouthpiece is located in a patient's mouth) and a second ridge is located on an exterior side of the mouthpiece 201 relative to a patient's teeth (e.g., located in front of a patient's teeth when the mouthpiece is located in a patient's mouth).

In various example embodiments, the mouthpiece 201 may include a plastic material configured to prevent damage to a patient's mouth (e.g., the patient's teeth) when inserted therein. Accordingly, the mouthpiece 201 may be sufficiently rigid to maintain its shape, but may be deformable such that the mouthpiece 201 locally deforms (e.g., dents, scratches, and/or the like), when contacting a rigid body part, such as a patient's teeth.

The mouthpiece 201 may have one or more gas channels configured to permit air to flow through the mouthpiece 201 extending therethrough. Although these gas channels are not shown in FIG. 3, various example embodiments comprise one or more gas channels as illustrated and described in reference to FIG. 4, which illustrates an alternative example embodiment of an oxygenation mask. The one or more gas channels may extend through the mouthpiece 201 from a front portion of the mouthpiece (e.g., proximate a second ridge) through a rear portion of the mouthpiece (e.g., proximate a first ridge). In various example embodiments, the gas channels are open to the air surrounding the mouthpiece 201, such that a patient may breathe air from the air surrounding the mouthpiece 201 through the one or more gas channels. In such embodiments, nozzles and/or other openings corresponding to each of the gas tubes may reside adjacent and/or within the one or more gas channels, such that at least a portion of a patient's breath is directed into the gas tubes and/or oxygen may be supplied from the gas tubes to the patient's mouth through the one or more gas channels.

In the illustrated example embodiment of FIG. 3, the mouthpiece 201 is secured relative to one or more gas tubes via a gas fitting 202. The gas fitting 202 places the one or more gas channels extending through the mouthpiece 201 in fluid communication with the one or more gas tubes such that the oxygen and carbon dioxide may be exchanged with the gas tubes through the gas channels extending through the mouthpiece 201. As noted above, the one or more gas channels of the mouthpiece may be open to the air surrounding the mouthpiece 201, and accordingly the gas fitting 202 may be configured to permit air to flow around the gas fitting 202 and through the gas chambers. In such configurations, the gas fitting 202 may be configured to place the one or more gas tubes in fluid communication with a stream of air entering and/or exiting the patient's mouth through the one or more gas channels. For example, if a gas tube provides oxygen (and/or oxygenated air) to the patient, oxygen from the gas tube is directed into the stream of air moving through the gas channels to supplement and/or enrich the oxygen content of atmospheric air breathed by the patient through the one or more gas channels. In various example embodiments, the gas fitting 202 includes one or more gas nozzles extending into the one or more gas channels of the mouthpiece 201 such that the one or more gas tubes are in fluid communication with the interior of the gas channels of the mouthpiece. Moreover, in various embodiments, one or more of the gas channels of the mouthpiece may be open to the surrounding environment and may not be in fluid communication with a portion of the gas fitting 202, and accordingly may provide an unobstructed path through which the patient may breathe.

In the illustrated example embodiment of FIG. 3, the gas tubes comprise an oxygen hose 209 and gas return hose 210 (also referred to herein as ETCO2 return hose 210). Like the oxygen hose 19 and gas return hose 20 described herein, an oxygen source 205 may be placed in fluid communication with the interior of the mouthpiece 201 via the oxygen hose 209 secured to the gas fitting 202. Accordingly, pressurized oxygen may be supplied to the patient through the mouthpiece 201 via the oxygen hose 209, from the oxygen source 205 secured to the gas fitting 202. Moreover, as shown in FIG. 3, the ETCO2 return hose 210 may additionally be secured to the mouthpiece 201 via the gas fitting 202. In various embodiments, the ETCO2 return hose 210 may place the interior of the mouthpiece 201 in fluid communication with an ETCO2 monitoring system 207 (also referred to herein as ETCO2 monitoring device 207) configured to monitor the lung metabolism of the patient. Although the illustrated example embodiment of FIG. 3 shows the ETCO2 return hose 210 being secured to the mouthpiece 201 via a common gas fitting 202 shared with the oxygen hose 209, some example embodiments may secure the gas return hose 210 via a separate gas fitting.

By providing an ETCO2 return hose 210 secured directly to the mouthpiece 201 such that at least a portion of a patient's breath may be captured within the gas return hose 210 and directed to an ETCO2 monitoring system 207, a patient's lung metabolism and/or partial pressure of carbon dioxide ($CO_2$) in a respiratory gas may be monitored without a separate monitoring device secured to the patient to collect the patient's breath. Indeed, a separate nasal cannula (which may impede access to a patient's nose) may not need to be provided for the patient in order to obtain a sufficient percentage of the patient's exhalation breath to accurately monitor the patient's lung metabolism rate. By providing the gas return hose 210 secured directly to the mouthpiece 201, a patient's comfort may be improved because additional monitoring devices may not need to be secured to the patient in addition to the mouthpiece 201.

As shown in FIG. 3, in an exemplary embodiment, the oxygen hose 209 and gas return hose 210 may be flexible and configured to be routed around a patient's ears in order to secure the oxygenation mask 200 to the patient. Moreover, the oxygenation mask 200 may additionally comprise a bolo 211 configured to secure the oxygen hose 209 and the gas return hose 210 relative to one another at a configurable location along the length of the hoses 209, 210. Accordingly, the bolo 211 may be moved along the length of the hoses 209, 210 to change the location at which the hoses 209, 210 are secured relative to one another. For example, while the mouthpiece 201 is placed within a patient's mouth and the hoses 209, 210 may be routed around the patient's ears, and the bolo 211 may be moved to a position along the length of the hoses 209, 210 proximate the patient's chin, such that the bolo 211 operates to secure the oxygenation mask 200 onto the patient while maintaining unobstructed access to the patient's nose.

Figure 4:
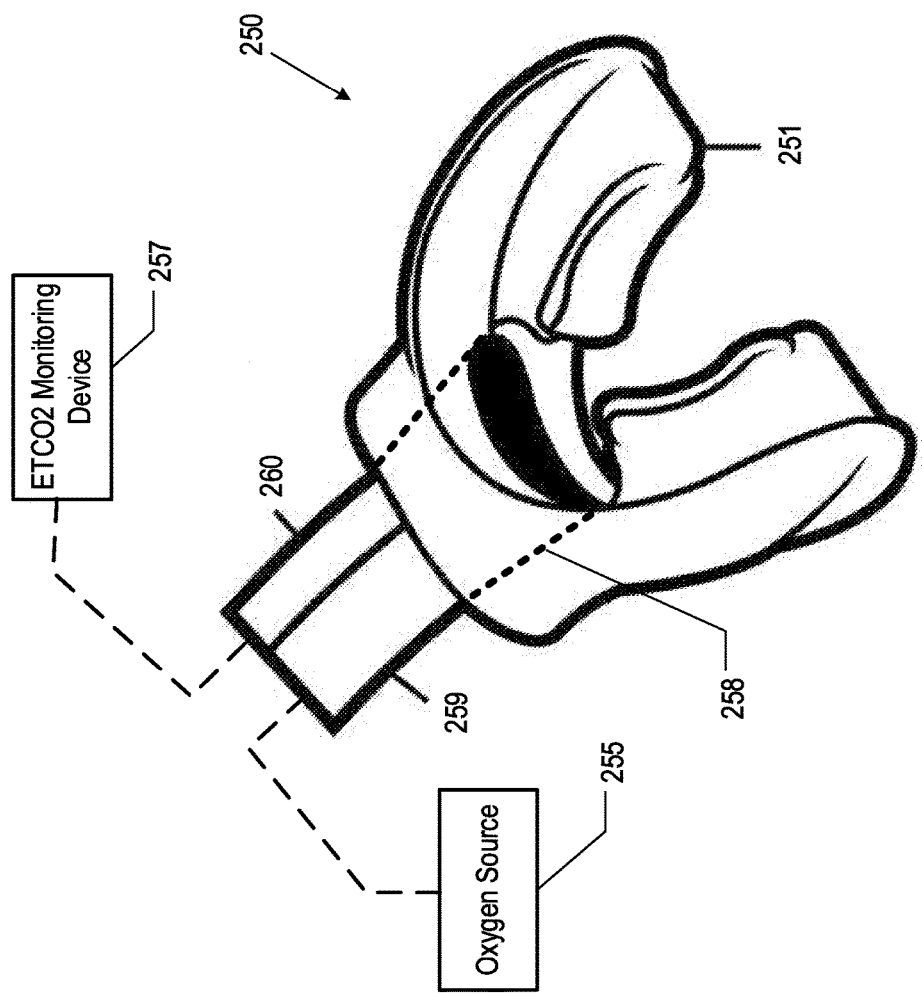
FIG. 4 shows an example oxygenation mask configured to provide unobstructed access to a patient's nose according to an exemplary embodiment.

With reference briefly to FIG. 4, which shows a perspective view of an example oxygenation mask 250, gas tubes (e.g., an oxygen hose 259 and a gas return hose 260 similar to those discussed herein) may be secured directly to a mouthpiece 251 having a configuration similar to mouthpiece 201 discussed herein. In such embodiments, a gas fitting may be integrated into the mouthpiece 251 to provide a direct connection between the gas tubes and the mouthpiece 251. In such embodiments, the gas tubes may be secured adjacent a gas channel 258 extending through the mouthpiece such that gases may flow between the gas tubes and the patient's mouth in order to supplement a patient's oxygen supply and/or to obtain a sample of a patient's exhaled breath. Accordingly, as discussed previously, the oxygen hose 259 may be connected to an oxygen source 255 and the gas return hose 260 may be connected to an ETCO2 monitoring device 257 such that oxygen may be supplied to the patient from the oxygen source 205, and a patient's exhaled breaths may be monitored by the ETCO2 monitoring device 207.

Moreover, although not shown in FIG. 4, the mouthpiece 251 may additionally define one or more ventilation ports to permit air from a surrounding environment to flow into and out of a patient's mouth. Similar to the example embodiments discussed herein, in such embodiments a patient may be permitted to breath air from a surrounding environment, and the gas tubes may be configured to supplement and/or enrich an oxygen supply of the inhaled air.

CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An oxygenation mask for monitoring a patient's breathing during a medical procedure, wherein the oxygenation mask comprises:
    a facial enclosure configured to enclose a patient's nose and mouth, wherein the facial enclosure comprises:
        a gas fitting detachably secured to the facial enclosure at a mid-portion of the facial enclosure such that the gas fitting aligns with the patient's nose and mouth, wherein the gas fitting defines a plurality of gas ports exiting the facial enclosure at the mid-portion of the facial enclosure;
        a hose fitting detachably secured in a stacked configuration with the gas fitting;
        a plurality of tubes terminating at the hose fitting, wherein each of the plurality of tubes are detachably secured to the hose fitting, the plurality of tubes comprising:
            an oxygen tube configured to supply oxygen gas received from an oxygen source to the patient via the facial enclosure; and
            an end-tidal carbon dioxide return tube configured to direct a portion of the patient's exhaled breath, comprising carbon dioxide, away from the facial enclosure and to an end-tidal carbon dioxide monitoring device to enable the end-tidal carbon dioxide monitoring device to detect an exhaled concentration or partial pressure of the carbon dioxide during the medical procedure;
    a first ventilation port and a second ventilation port, wherein the first ventilation port and the second ventilation portion are positioned on opposite lateral sides of the facial enclosure and wherein each of the first ventilation port and the second ventilation port comprises a one-way valve secured therein and configured to:
        allow gas to pass out of the facial enclosure to a surrounding environment while preventing gas to pass into the facial enclosure through the first ventilation port and the second ventilation port; and
        permit a portion of the patient's exhaled breath to exit from within the facial enclosure; and
    a first access port and a second access port each configured to permit an object to be passed into the interior of the facial enclosure in an instance in which the oxygenation mask is positioned over the patient's face, wherein the first access port and the second access port are positioned on the opposite lateral sides of the facial enclosure below and outward from the first ventilation port and the second ventilation port and each of the first access port and the second access port extend through a side portion of the facial enclosure;
    one or more plugs corresponding to each of the one or more access ports, wherein each plug is detachably secured relative to the oxygenation mask and is configured to selectably engage a perimeter of a corresponding access port to block the access port; and
    wherein the tube engagement member is configured to detachably secure the plurality of tubes to the facial enclosure such that each of the plurality of tubes are aligned with the patient's nose and mouth and are in fluid communication with the interior of the facial enclosure.

2. The oxygenation mask of claim 1, wherein:
    the oxygen tube is connected to the end-tidal carbon dioxide return tube along a portion of a length of the oxygen tube.

3. The oxygenation mask of claim 1, wherein:
    the tube engagement member corresponds to a single gas port extending through the facial enclosure, and wherein the oxygen tube and the end-tidal carbon dioxide return tube are both in fluid communication with an interior of the oxygenation mask through the single gas port.

4. The oxygenation mask of claim 1, wherein the object comprises an endoscope or another medical device.

5. The oxygenation mask of claim 1, wherein:
    the tube engagement member is positioned on the facial enclosure such that the tube engagement member is below the patient's nose in an instance in which the facial enclosure is secured on the patient's face.

6. The oxygenation mask of claim 1, wherein:
    the tube engagement member is positioned on the facial enclosure closer to a bottom portion of the facial enclosure than a top portion of the facial enclosure.

7. The oxygenation mask of claim 1, wherein the medical procedure comprises an anesthesia procedure performed on the patient.

8. An oxygenation mask for monitoring a patient's breathing during a medical procedure, wherein the oxygenation mask comprises:
    a facial enclosure configured to enclose a patient's nose and mouth, wherein the facial enclosure comprises:
        a gas fitting detachably secured to the facial enclosure at a mid-portion of the facial enclosure such that the gas fitting aligns with the patient's nose and mouth, wherein the gas fitting defines a plurality of gas ports exiting the facial enclosure at the mid-portion of the facial enclosure;
        a hose fitting detachably secured in a stacked configuration with the gas fitting;
        an inflatable oxygen storage bag secured to the hose fitting and in fluid communication with an interior of the facial enclosure and configured to inflate when oxygen is flowing into the mask via an oxygen tube, wherein unused oxygen collects in the oxygen bag;
        a plurality of tubes, wherein each of the plurality of tubes are detachably secured, and wherein the plurality of tubes comprises:
            an oxygen tube configured to supply oxygen gas received from an oxygen source to the patient via the facial enclosure, wherein the oxygen tube terminates at the gas fitting; and
            an end-tidal carbon dioxide return tube configured to direct a portion of the patient's exhaled breath, comprising carbon dioxide, away from the facial enclosure and to an end-tidal carbon dioxide monitoring device to enable the end-tidal carbon dioxide monitoring device to detect an exhaled concentration or partial pressure of the carbon dioxide during the medical procedure, wherein the end-tidal carbon dioxide return tube terminates at the hose fitting; a first ventilation port and a second ventilation port, wherein the first ventilation port and the second ventilation port are positioned on opposite lateral sides of the facial enclosure and wherein each of the first ventilation port and the second ventilation port comprises a one-way valve secured therein and configured to:

allow gas to pass out of the facial enclosure to a surrounding environment while preventing gas to pass into the facial enclosure through the first ventilation port and the second ventilation port; and permit a portion of the patient's exhaled breath to exit from within the facial enclosure; and a first access port and a second access port each configured to permit an object to be passed into the interior of the facial enclosure in an instance in which the oxygenation mask is positioned over the patient's face, wherein the first access port and the second access port are positioned on the opposite lateral sides of the facial enclosure below and outward from the first ventilation port and the second ventilation port and each of the first access port and the second access port extend through a side portion of the facial enclosure;

one or more plugs corresponding to each of the one or more access ports, wherein each plug is detachably secured relative to the oxygenation mask and is configured to selectably engage a perimeter of a corresponding access port to block the access port; and wherein the tube engagement member is configured to detachably secure the plurality of tubes to the facial enclosure such that each of the plurality of tubes are in fluid communication with the interior of the facial enclosure.

\* \* \* \* \*